United States Patent [19]

Finlan

[11] Patent Number: 5,023,053
[45] Date of Patent: Jun. 11, 1991

[54] BIOLOGICAL SENSORS

[75] Inventor: Martin F. Finlan, Aylesbury, England

[73] Assignee: Amersham International PLC, Little Chalfont, England

[21] Appl. No.: 355,187

[22] Filed: May 22, 1989

[30] Foreign Application Priority Data

May 20, 1988 [GB] United Kingdom ............. 8811919

[51] Int. Cl.$^5$ ............. G01N 21/00; G01N 21/55; G01J 3/30
[52] U.S. Cl. ............. 422/82.05; 422/82.11; 422/66; 422/68.1; 356/318; 356/445
[58] Field of Search ............. 422/82.05, 58, 66, 98; 356/318, 445

[56] References Cited

U.S. PATENT DOCUMENTS

| Re. 30,627 | 5/1981 | Bagshawe et al. | 422/66 |
| 3,526,480 | 9/1970 | Findl et al. | 422/66 |
| 4,844,613 | 7/1989 | Batchelder et al. | 356/445 |
| 4,857,273 | 8/1989 | Stewart | 422/82.05 |
| 4,877,747 | 10/1989 | Stewart | 422/82.11 |
| 4,883,642 | 11/1989 | Bisconte | 422/66 |
| 4,889,427 | 12/1989 | Van Veen et al. | 356/445 |

Primary Examiner—Robert J. Warden
Assistant Examiner—Theresa A. Trembley
Attorney, Agent, or Firm—Wenderoth, Lind & Ponack

[57] ABSTRACT

A surface plasmon resonance (SPR) sensor in which a membrane is used to enable the sensitive material to be readily changed to enable tests to be carried out on a sequential basis simply by moving or changing the membrane. In one embodiment, the membrane takes the form of a continuous film (24) which lies against and is moveable across by means not shown, a transparent plate (17) which forms part of the SPR sensor. The film (24) comprises a layer (31) of flexible transparent material to which is applied a thin layer (32) of metal such as silver. Applied to layer (32) is a layer (33) of sensitive material. The final layer (34) is a preformed layer of hydrophyllic plastics material which incorporates troughs (37) and passageways (35,38) for the transfer of sample across the sensitive layer. Light from a laser (not shown) is subject to total internal reflection at the interface between the transparent layer (31) and metal layer (32), and the reflected light is collected by a light detector (not shown). Provided conditions are correct, surface plasmon resonance occurs at the area of total internal reflection, the characteristics of which resonance are sensitively dependent upon the reaction between the sample and the sensitive layer.

13 Claims, 6 Drawing Sheets

BIOLOGICAL SENSORS

This invention relates to sensors for use in biological, biochemical and chemical testing and in particular to immunosensors used to monitor the interaction of antibodies with their corresponding antigens.

When antibodies are immobilised on a surface, the properties of the surface change when a solution containing a corresponding antigen is brought into contact with the surface to thus allow the antigen to bind with the antibody. In particular, the change in the optical properties of the surface can be monitored with suitable apparatus.

The phenomenon of surface plasmon resonance (SPR) can be used to detect minute changes in the refractive index of the surface as the reaction between the antigen and the antibody proceeds. Surface plasmon resonance is the oscillation of the plasma of free electrons which exists at a metal boundary. These oscillations are affected by the refractive index of the material adjacent the metal surface and it is this that forms the basis of the sensor mechanism. Surface plasmon resonance may be achieved by using the evanescent wave which is generated when a light beam is totally internally reflected at the boundary of a medium, e.g. glass, which has a high dielectric constant. A paper describing the technique has been published under the title "Surface plasmon resonance for gas detection and biosensing" by Lieberg, Nylander and Lundstrom in Sensors and Actuators, Vol. 4, page 299. Illustrated in FIG. 1 of the accompanying drawings is a diagram of the equipment described in this paper. A beam 1 of light is applied from a laser source (not shown) onto an internal surface 2 of a glass body 3. A detector (not shown) monitors the internally reflected beam 4. Applied to the external surface 2 of glass body 3 is a thin film 5 of metal, for example gold or silver, and applied to the film 5 is a further thin film 6 of organic material containing antibodies. A sample 7 containing antigen is brought into contact with the antibody film 6 to thus cause a reaction between the antigen and the antibody. If binding occurs the refractive index of the layer 6 will change owing to the increased size of the antibody molecules and this change can be detected and measured using the surface plasmon resonance technique, as will now be explained.

Surface plasmon resonance can be experimentally observed, in the arrangement of FIG. 1, by varying the angle of the incident beam 1 and monitoring the intensity of the internally reflected beam 4. At a certain angle of incidence the parallel component of the light momentum will match with the dispersion for surface plasmons at the opposite surface 8 of the metal film. Provided that the thickness of metal film 5 is chosen correctly there will be an electromagnetic coupling between the glass/metal interface at surface 2 and the metal/antibody interface at surface 8 which results in surface plasmon resonance and thus an attenuation in the reflected beam 4 at that particular angle of incidence. Thus, as the angle of incidence of beam 1 varied, surface plasmon resonance is observed as a sharp dip in the intensity of the internally reflected beam 4 at a particular angle of incidence. The angle of incidence at which resonance occurs is affected by the refractive index of the material against the metal film 5—i.e. the antibody layer 6—and the angle of incidence corresponding to resonance is thus a direct measure of the state of the reaction between the antibody and the antigen. Increased sensitivity can be obtained by choosing an angle of incidence half way down the reflectance dip curve, where the response is substantially linear, at the beginning of the antibody/antigen reaction, and then maintaining that angle of incidence fixed and observing changes in the intensity of the reflected beam 4 with time.

Known systems of the type described with reference to FIG. 1 utilise a prism as the glass body 3. A diagram showing this arrangement is given in FIG. 2 which is simply an experimental set up intended to demonstrate surface plasmon resonance. The prism is shown under reference 8 and has applied to its undersurface a thin film 5 of metal. Light 1 from a laser source (not shown) is incident on the prism where it is refracted at point 9 before entering the prism. The internally reflected beam 4 is likewise refracted (at point 10) upon exiting from the prism.

The present invention utilises an alternative method of obtaining surface plasmon resonance in which a membrane is used in order to achieve the necessary internal reflection. The membrane takes the form of a laminate which comprises, in its most basic form, a first film made of transparent material and used, in effect, to replace the prism of FIG. 2 in order to obtain the internal reflection needed for surface plasmon resonance, a second film of metal, such as silver, and a third film of sensitive material such as an antibody layer, the layers being arranged in the manner of FIG. 1—i.e. first film—second film—third film.

The great advantage of using such an arrangement is that the membrane can be produced very cheaply and is thus readily available without great expense. The membrane can be supplied in the form of a continuous film, possibly sprocket fed like a cinematograph film, so that new areas of membrane can be brought into play in sequence one after another. Such a film could be packaged in cassette form.

The concept of using a thin film as the transparent medium for producing internal reflection is based on the curves shown in FIG. 3 of the accompanying drawings which are derived from the optical geometry shown in FIG. 4 of the accompanying drawings.

In FIG. 4 there is shown a diagrammatic representation of the reflection and refraction of an input light wave 11 travelling in a medium having a refractive index n1 in a thin block 12 of transparent material having a refractive index n2. On the back surface of the block 12 is formed a layer 13 of material such as silver. The refractive index of the medium behind the silver is n3. The graph of FIG. 3 shows the percentage of transmission or reflection at the interfaces n1/n2/n3 for both S- polarised light and for P- polarised light as the angle 0, of incidence is varied.

It is P- polarised light with which the present invention is concerned since this has an electric field component normal to the surface. It will be seen that, in the region of total internal reflection (100% reflection) from the interface n2/n3, the transmission at the interface n1/n2 is better than 90% up to an angle $\theta_1$ of 70°. This spans the angle of minimum reflection of a useful surface plasmon resonance system of about 63°. It is clear therefore that the geometry shown in FIG. 4 is feasible and it will be seen that a membrane like "block" in place of the block 12 would exhibit a like effect.

One problem which is immediately apparent from FIG. 4 is that, as the angle of incidence changes, the position on the interface n2/n3 at which the incoming beam is incident will likewise vary. Because of inevitable variations in the metal film 13 and in any sensitive (e.g. antibody) coating applied thereto, the angle of incidence at which the surface plasmon resonance effect is exhibited changes as this movement occurs, which in turn introduces a further variable factor into the measurement, and reduces accuracy.

For this reason, it is proposed to provide means for ensuring that the point at which incidence at the interface n2/n3 occurs remains stationary whatever the angle of incidence within the likely range of angles of incidence. This can be achieved by means of a specially shaped concave reflecting element, as will be described later.

In order to monitor the dip which occurs at resonance, it is necessary to illuminate the interface n2/n3 over a range of angles about the resonant angle of incidence which is normally about 63°. There are two approaches: in the first a wide section solid beam is focused to a point on the interface in such a way that the incoming beam spans a range of angles about resonance. This type of arrangement is described in more detail in our European patent application No. 0305109. In a second approach, a relatively narrow beam is scanned about a range of angles close to the angle of incidence corresponding to resonance. This scanning may be achieved using a mirror in conjunction with a concave reflector. The mirror is caused to oscillate backwards and forwards at, say 50 Hz and takes the light output from the light source to move the beam backwards and forwards in sympathy in a scanning motion. The scanning beam is applied to the concave reflector which reflects the beam to a fixed spot on the n2/n3 interface whatever the angle of scanning. As an alternative, the mirror is caused to rotate continuously at, say, 50 r.p.s. to produce a 360° output sweep of the light beam. All but a small arc of interest is masked off to thereby produce, after reflection, an undirectional scanning motion across the angles of incidence spanning resonance. These techniques are described in more detail in our copending European Patent Application No. 89304570.8.

In a system using a membrane in the form of a continuous film a difficulty arises in the sample feeding arrangement since it is essential that the samples used in tests are not contaminated by residue left over from previous tests. If a fixed sample feeding arrangement is used, with the samples being fed one after another through a common feeding means then, in order to avoid cross contamination, some form of inter-test rinsing and/or cleaning would be necessary. This, whilst possible, could lead to additional complications and expense, and we accordingly prefer to incorporate the sample feeding arrangements actually within the membrane itself. This concept can be incorporated in both continuous film membranes, and for non-continuous membranes which may nevertheless be moved along to carry out a plurality of tests one after the other. Membranes of this latter type could be provided in the form of small card-like membranes, perhaps a few centimetres long.

The sample feeding arrangements are provided within the membrane by incorporating a further layer in the laminate structure making up the membrane. This further layer is applied to the aforesaid third film—the sensitive layer—so that, in operation, a sample fluid can be brought into contact with the sensitive layer to effect a reaction between the sample and the sensitive layer.

For example, said further layer may be of porous material, which is used by placing the sample on its side remote from the sensitive layer, and allowing the sample to pass through the porous layer and into the sensitive area in a reasonably controlled manner. A particularly suitable form of porous material is that marketed by Anotec Separations Limited. This comprises a non-flexible honeycomb filter fabricated from alumina. The filters have a plurality of 200 nm diameter apertures passing from one face to the other in a honeycomb-like structure. In some versions, one side of the 200 nm diameter apertures are terminated on one side by 20 nm apertures. This type of filter has the inherent advantage of providing a filter to preven cells and other large particles within the sample from reaching the active area.

If an alternative embodiment, said further layer takes the form of a structural layer, pre-formed to provide controlled feeding of the sample, or a plurality of samples simultaneously, past the active area. In one embodiment, the further layer comprises a film of material having passage means extending from its face remote from the sensitive layer to the opposite face. In order to provide for the flow of sample past the active area, as distinct from the sample simply remaining stationary when it reaches the active area, it is preferred to incorporate in the aforesaid further layer in absorbent material which will be operable to draw the sample past the active area, at least for the short period of the test. Thus, the arrangement is such that said passage means leads from the face remote from the sensitive area, past the sensitive area, to the absorbent material. Preferably the film making up said further layer is made from hydrophyllic material.

In practice it may be desired to carry out a plurality of tests simultaneously. This could be in order for speed, or in order to compare the results from a sample or samples with a reference under identical conditions. Such simultaneous testing may involve more than one sample or may involve several simultaneous tests on a single sample. The number of simultaneous tests to be carried out, and the manner of carrying out the tests will dictate the exact way in which the passage means is constructed. For example, in order to carry out a single test on a single sample, the passage means could comprise a single aperture passing through from one face of said further layer to the other. If an absorbent material is included, the aperture may open, at its end adjacent the sensitive layer, into another aperture leading to the absorbent material. This is used by introducing sample to the aperture at its end remote from the sensitive area and allowing the sample to pass through the aperture to the sensitive area and on, if appropriate, to the further aperture to the absorbent material. That end of the aperture which opens into the face of the further layer remote from the sensitive layer may be chamfered in order to assist addition of sample to the aperture. It will be seen that such chamfering defines a well into which a reasonably accurate amount of sample can be placed for the test. Preferably, the aperture and the further aperture if fitted, are of a size such that the sample travels along them by capillary action.

It is desired to test a plurality of separate samples simultaneously, it will be seen that a plurality of such separate apertures could be provided, spaced apart about the surface of the further film. Associated with each such aperture will be a separate sensitive layer so that separate tests could be carried out on each sample at a separate and distinct sensitive area. The point of incidence of the light on the glass/metal interface is caused to scan across all such areas which are required to be tested simultaneously so as to enable a picture to be built up of the separate tests. Where an absorbent material is used in order to draw sample continuously past the active areas during the course of the tests, these may be provided as separate pieces of absorbent material for each test or, bearing in mind that the absorbent material for each test or, bearing in mind that the absorbent material is on the downstream side of the active areas, could be formed as a single piece of absorbent material common to a plurality of active areas.

If it is desired to carry out multi-analyte testing of a single sample, then a plurality of separate active areas need to be provided, as above. However, the sample feeding arrangements need to be such as to enable a single sample to be applied simultaneously to the various active areas. In this case, the passage means may take the form of a slot-like aperture passing from one face to the other of said further layer. Preferably, as before, the edges of the slot where they open onto the face which is remote from the sensitive layer are preferably chamfered to define an elongate through-like well into which sample can be placed for the test. The sample passes down the slot to the opposite face of the further layer where it reacts with the various sensitive area which are positioned to lie at the bottom of the slot. Preferably the size of the slots is such that the sample passes through it by capillary action. Absorbent material may be used, as before to draw the sample past the active areas.

In order to carry out multiple testing of any sort, means must be provided for moving the point of incidence of the light beam across the various active areas. This can take the form of single or multiple line scanning of the point of incidence and is achieved by the use of mirrors moved by suitable motors. This is discussed in more detail in our aforementioned European Patent Application No. 89304570.8.

Although the layer applied to the metal film is described herein as an antibody layer for use in immunoassays, it will be seen that any sensitive layer whose refractive index changes upon an event occurring can be used thus to provide a sensitive detector having a wide variety of applications in the fields of biology, biochemistry and chemistry. The material comprising the sensitive layer may be specific to a particular entity within the sample or may be nonspecific (i.e. may interact with several species of entity within the sample). Examples of specific materials include recognition molecules such as the aforementioned antibodies which will specifically bind an analyte of interest within the sample, DNA/RNA probes which will bind with their complements in the sample liquid, or lectins, glycoproteins or enzyme substrates, all of which are capable of recognising and binding with the other partner in a bimolecular recognition pair.

Examples of non-specific materials include hydrophobic materials, for example in the form of a monolayer of phospholipid-type molecules to capture amphipathic molecules, or hydrophilic materials which would capture polysaccharides. Indeed, it has been found that the surface of the metal film itself can form an effective non-specific binding material. Silver or gold surfaces will bind proteins or polynucleotides such as DNA or RNA without the need for any further coating and, in this case, a separate sensitive layer is effectively dispensed with altogether, and the surface of the metal film used directly for the capture of entities within the sample to be tested.

The metal film material is commonly silver or gold, usually applied by evaporation. The film needs to be as uniform as possible in order to cater for minute movement in the point of incidence of the incoming beam. It is assumed that a structural metal film will give the best resonance and there are various ways in which the transparent film can be pretreated to improve the performance of the metal film and in particular to control the natural tendency of such films to form discontinuous islands:

1. Immersion in molten metal nitrates and other molten salts. This has the effect of introducing ions into the surface in a manner which can be structured and which can act as foci for island formation.
2. Ion bombardment to introduce nucleating sites. The removal of the more mobile ions has been demonstrated to reduce the thickness at which the evaporated film becomes continuous.
3. Electroless plating or electroplating over lightly evaporated films (0 to 100 angstroms thick). Electroless plated films survive to a greater thickness than evaporated films and could form more stable nuclei for subsequent coating.
4. Evaporating onto electroless plated films. The electroless plated films have a stronger tendency to an island structure and to bigger islands with greater spacing than evaporating films. This could be of advantage in tuning to light of a prescribed wavelength.

Coating performance can also be improved by:
1. Controlling the surface temperature during coating. Using a higher temperature substrate increased the islands' size and the spacing between them and conversely.
2. Evaporating in the presence of a magnetic or electrostatic field or electron emission device to control the ion content of the vapour stream. The state of charge of the substrate is known to affect the island structure.
3. Controlling the angle of incidence of the evaporated vapour stream relative to the film surface. The mobility of the evaporated atoms and hence their ability to form bigger islands is greater when the momentum of the atoms relative to the film surface is increased.

In order that the invention may be better understood, several embodiments thereof will now be described by way of example only and with reference to the accompanying drawings in which.

Figure 5:
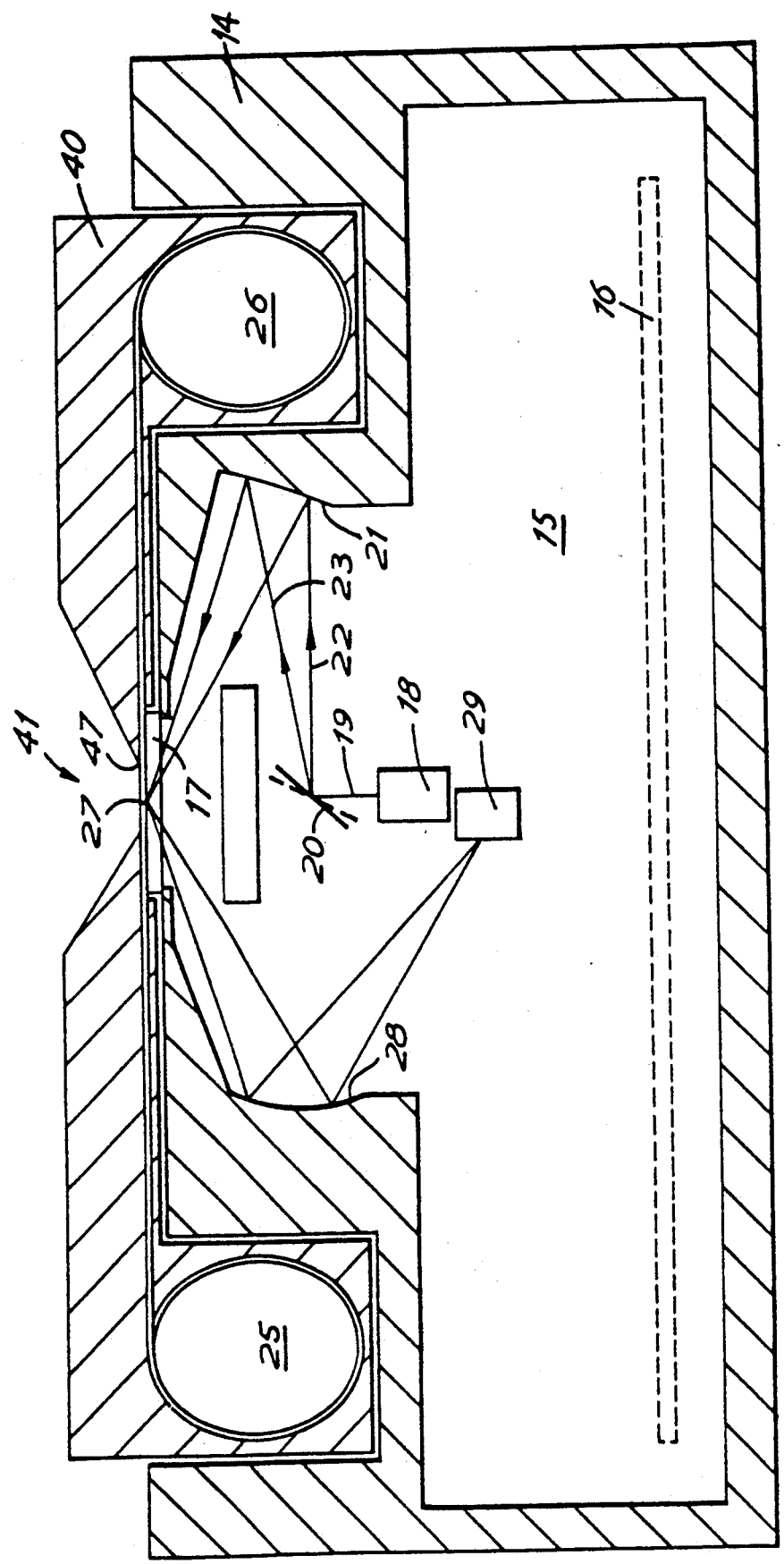
FIG. 5 is a diagrammatic side view of an embodiment of a sensor according to the present invention.

Referring to FIG. 5, the apparatus comprises a housing 14 having a hollow interior 15 in which is positioned a printed circuit board 16 on which is mounted the electronic circuitry associated with the apparatus. An aperture is formed in the top part of the housing, which aperture is covered by a support plate 17 of transparent material.

A radiation source 18 produces a collimated input beam 19 of electromagnetic radiation. The frequency of the radiation must be such as to result in the generation of surface plasmon waves and in practice will be within or near the visible region. Suitable sources include a helium neon laser or an infra red diode laser, but an ordinary light source, with suitable filters and collimators, could be used.

The light beam 19 is applied to a mirror 20 which in turn directs the light onto a concave reflecting surface 21 and thence to the transparent support plate 17. The mirror 20 is driven by motor means (not shown), to rotate in an oscillatory manner between the limit positions shown by the solid and dotted lines. The result of this is that the light beam applied to the reflecting surface 21 scans backwards and forwards between the positions represented by the beams 22 and 23.

Positioned in the top surface of the support plate 17 is a membrane in the form of a continuous film 24 which is moveable from left to right in FIG. 5 from a supply reel 25 to a take-up reel 26. In its simplest form, the membrane takes the form of a layer of flexible transparent material to which is applied a metal film layer for example of silver and a final layer of sensitive material, such as an antibody layer. The arrangement is such that the layers are in the order—transparent support plate 17—flexible transparent layer—metal film layer—sensitive layer. Thus the sensitive layer is on the top when seen in FIG. 5. In practice the sample feeding arrangements dictate a more sophisticated construction of film, an example of which is given in FIG. 6, to which reference will shortly be made.

Figure 1:
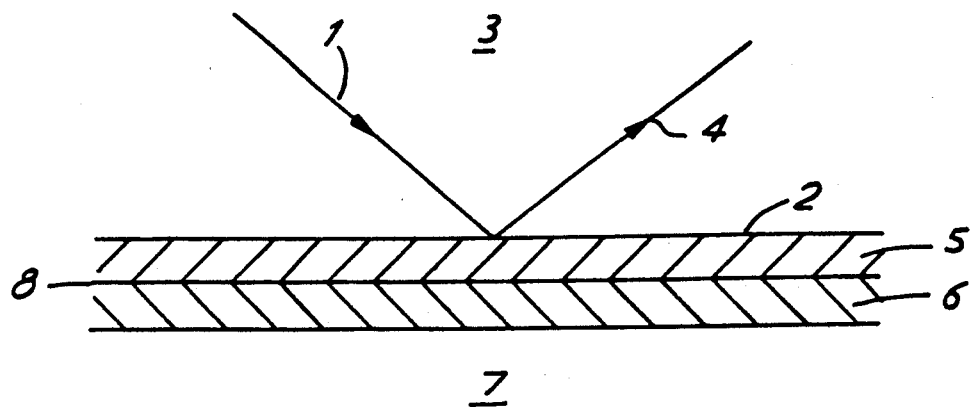
FIGS. 1 and 2 are diagrams of known experimental arrangements for demonstrating the surface plasmon resonance effect.
Figure 2:
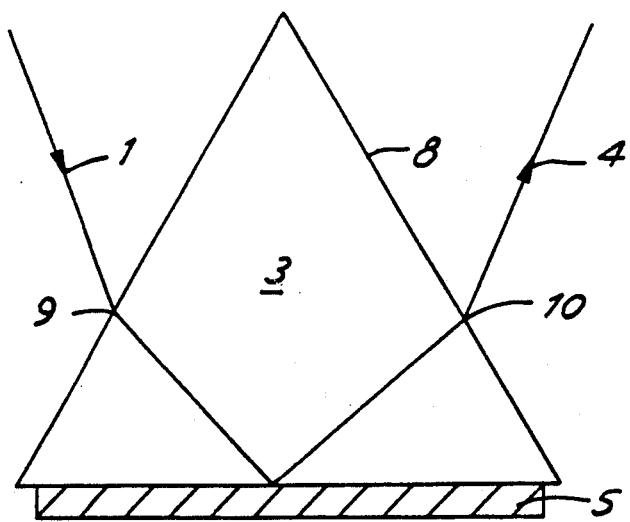
Figure 3:
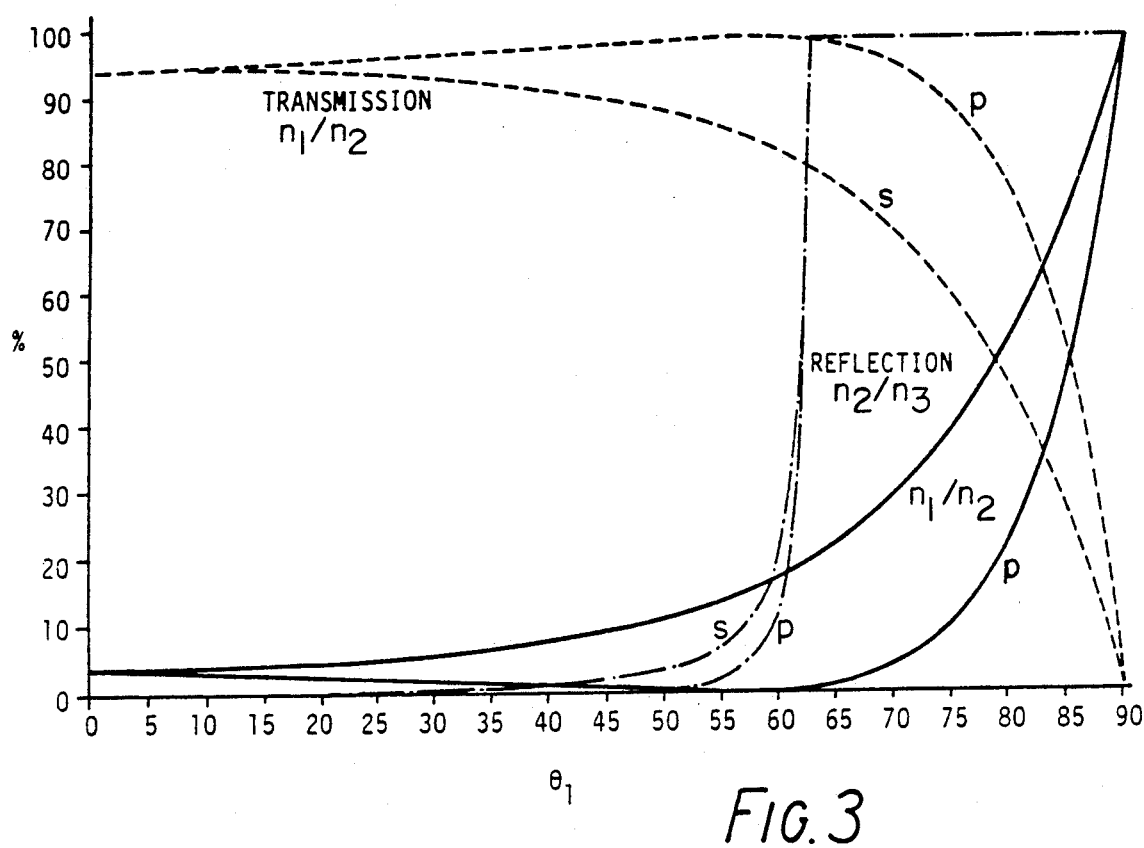
FIG. 3 is a graph of percentage transmission or reflection of light against angle of incidence 01.
Figure 4:
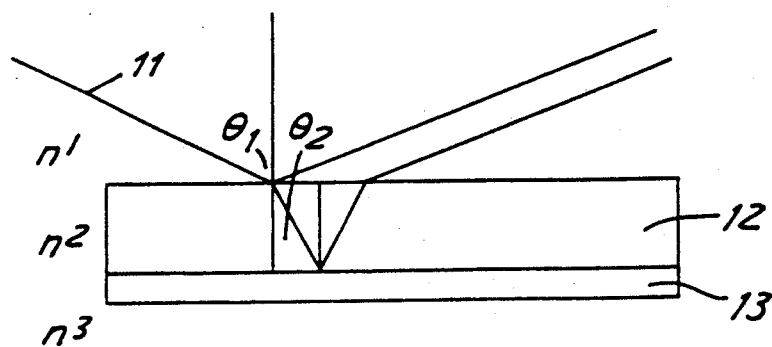
FIG. 4 is an example of thin film optical geometry used to enable interpretation of the graph of FIG. 3.

It will be noted that the flexible transparent layer lies directly against the transparent plate, possibly with an optical coupling fluid in between. Preferably the refractive index of the plate 17 is the same as that of the flexible transparent layer so that the two effectively act as a single transparent block, as far as light is concerned. Light incident from reflecting surface 21 behaves in the block in a similar manner to that described above with reference to FIGS. 3 and 4. The metal film layer causes the light to be internally reflected at a point 27 lying on the interface between the flexible transparent layer and the metal film layer of the film 24. The internally reflected light passes out of the block, and is reflected off a further concave reflecting surface 28 to be incident on the sensitive surface of a light detector 29.

The reflective surface 21 has a shape which is such as to bring light incident thereon from a range of angles to a single point 27, despite the refraction which inevitably occurs when the light enters the transparent plate 17. Computer analysis of the ray paths can derive a suitable shape for surface 21 to ensure that point 27 is stationary as the scanning between limit positions 22, 23 occurs. Likewise, reflective surface 28 has a shape which is such as to bring light incident thereon from a range of angles to a single point at the sensitive area of detector 29.

The reflector surfaces 21, 28 are formed by machining of the material, for example aluminum, of the housing 14. If the housing is not fabricated from a suitable material, the reflective surfaces 21, 28 can, of course, be formed as separate elements attached to the housing. Diamond machining of aluminium results in a highly reflective surface whose shape can be tailored, under computer control, to give whatever optical characteristics are required of it.

Provided that the conditions are correct and, in particular, that the angle of incidence of the incoming beam at the interface between the flexible transparent layer and the metal film layer is correct, then surface plasmon resonance will result, causing a dip in the intensity of the internally reflected light as the angle of incident of the incoming wave is scanned by the mirror 20. A picture of the whole dip can thus be built up by the detector 29 by relating the detector output, on a time basis, with the scanning movement of the mirror 20. This is carried out in the associated electronic circuitry and, since it does not particularly concern the present invention, will not be described further.

The sensitive layer is one whose refractive index changes as it reacts with a sample, in the manner described above. This changes the angle of incidence at which surface plasmon resonance occurs, and thus the reaction of a sample with the sensitive layer can be monitored by observing the dip as the test proceeds. In order to carry out a test, it is simply necessary to place a sample to be tested on top of the sensitive layer in the area of the point 27 at which the light is incident, and observe the changes in the dip characteristics.

Figure 6:
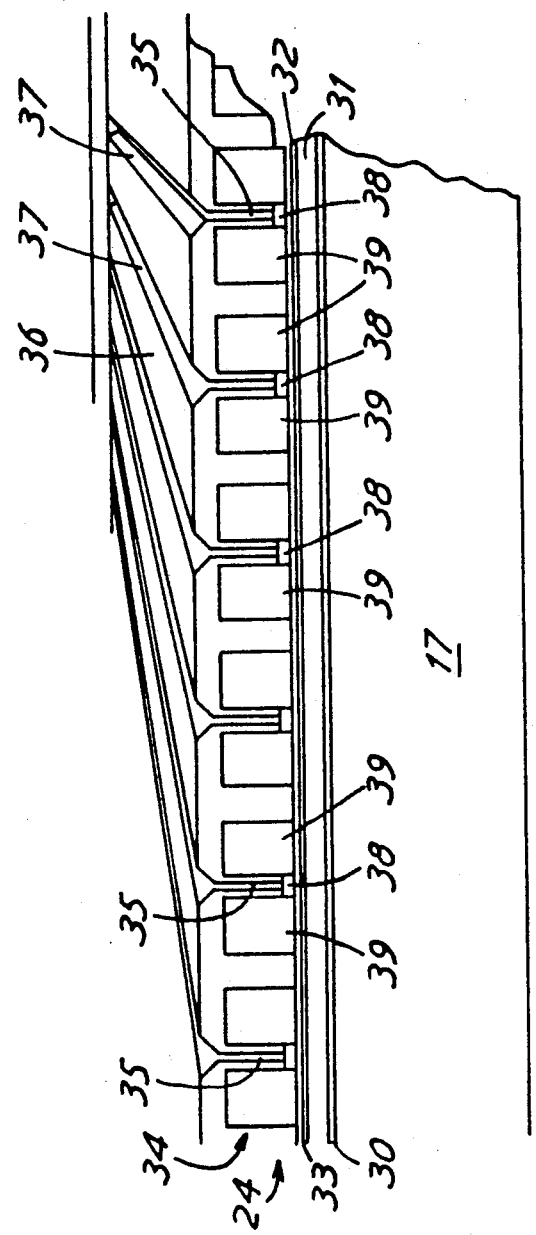
FIG. 6 is an enlarged perspective view showing detail of the membrane construction.

A particular method of feeding the sample to the active layer is shown in FIG. 6 to which reference will now be made. The film 24 which is shown in FIG. 6 is able to carry out multiple analyte testing on a single sample and, for this purpose, the point 27 at which light is incident on the interface between the flexible transparent layers and the metal film layer, which point was hitherto assumed to be stationary, must in fact by moveable in a direction transverse to the plane of FIG. 5. This is achieved by means of a more sophisticated mirror system than that shown at 20 in FIG. 5, and is described in greater detail on our aforementioned copending application.

In FIG. 6, the film 24 is shown lying against the transparent plate 17 with an optional layer 30 of optical coupling gel or fluid in between. The film 24 comprises a layer 31 of flexible transparent material, such as transparent plastic material to which is applied a thin flim layer 32 of metal such as silver or gold. Applied to the layer 32 is a layer 33 of sensitive material such as an antibody layer. The layer 33 may be continuous, or may be applied in discrete areas where the reactions occur, as will become clear hereinafter. The final layer, shown under reference 34 is a preformed layer of, preferably hydrophyllic, plastics material which is used for feeding the sample to the sensitive layer 33 so as to react therewith.

The layer 34 has a plurality of slots 35 extending transversely across the layer. The slots open into the top surface 36 of layer 34, and their edges are chamfered at 37 to define elongate troughs into which sample to be tested may be placed. The slots do not extend right through the layer 34, but terminate in a plurality of transverse passages 38 formed in that surface of layer 34 which faces the sensitive layer 33. Each transverse passage defines a chamber which becomes, during a test, the active area where the reaction between the sample and the sensitive layer 34 takes place. Each slot 35 terminates in a plurality of separate passages 38 which thus define a plurality of spaced active areas in which separate tests on a common sample can be carried out. Each slot 35 is associated with a pair of absorbent areas 39, formed as respective channels opening into the undersurface of layer 34 and containing an absorbent material. The passages 38 are such as to lead into the absorbent areas 39 so as to draw the sample continuously across the active area during a test.

In order to use the apparatus, the film 24 is advanced until one slot 35 lies in registry with the point 27. A sample to be tested, and containing an antigen capable of binding with the antibody molecules in layer 33 is placed in the well 37 and passes through slot 35 by capillary action. Emerging from slot 35, the liquid sample commences to flow rapidly outwards in opposite directions along passageway 38 towards the absorbent material 39, passing as it does so, the layer 33. The sample adjacent the layer 33 is thus being constantly replenished during the course of the test, which ensures maximum sensitivity.

As the sample flows past the layer 33 any antigen within the sample capable of binding with the antibody in layer 33 will do so, thus altering the refractive index of layer 33 as the reaction proceeds. This change in refractive index in continuously monitored during the test by directing at the point 27 the light beam from source 18. Provided that conditions are correct—in particular the angle of incidence at the point 27 is correct—the application of the light beam will result in the generation of a plasmon wave, thus extracting energy from the input beam and causing an attenuation in the intensity of the output beam at a particular angle of incidence. The mirror 20 is oscillated backwards and forwards as the test proceeds so as to cause the beam to scan between the limit positions 22, 23, as explained above. These limit positions are such as to cover the dip caused by the attenuation in the output beam. The circuitry controlling the mirror motor outputs a strobe signal to enable the detector 29 to identify the instantaneous angle at which the light is incident at the point 27, so that an accurate picture of the reflectance dip can be obtained.

The mirror 20 is also moved in such a way as to cause the point 27 to itself move backwards and forwards across the film 24 so as to pass one by one over the various active areas beneath the slot 35. The movement of point 27 may be continuous, but preferably the arrangement is such that the point 27 hovers over each active area for a short time before passing on to the next so as to enable the dip to be scanned over each active area. Suitable strobe signals output from the mirror motor drive circuitry are synchronised with the output from detector 29 so that the output from detector 29 can be identified with a particular active area along the slot 35.

The initial reflective dip which is chosen for setting up the limit beams 22, 23 may be taken from the dip which results when some neutral or buffer solution is passed through the cell but before any reaction thereof has taken place. In connection with the latter method, it is to be noted that, as sample begins to flow through the active area adjacent layer 33 the refractive index does not start to change immediately due to the antibody/antigen reaction. There is thus sufficient time to take an initial reading with the unreacted sample flowing past, which reading can be utilised, using feedback circuitry, to rapidly adjust the mirror 20 so that the centre angle of incidence between that of the limit beams 22, 23 can be chosen correctly. This centre angle may be chosen to be the actual angle of dip, or it may be an angle half way down the reflectance dip.

When each test is completed, the film 24 may be advanced by an amount equal to the distance between adjacent slots 35, thereby to bring the next slot into line with the point 27, and thus enable a further test to be carried out. This process can be repeated until the film 24 runs out.

It is preferred to provide the film 24 housed in a disposable cassette 40 (FIG. 5) which incorporates an opening 41 via which sample may be placed in the wells of the exposed film.

Figure 7:
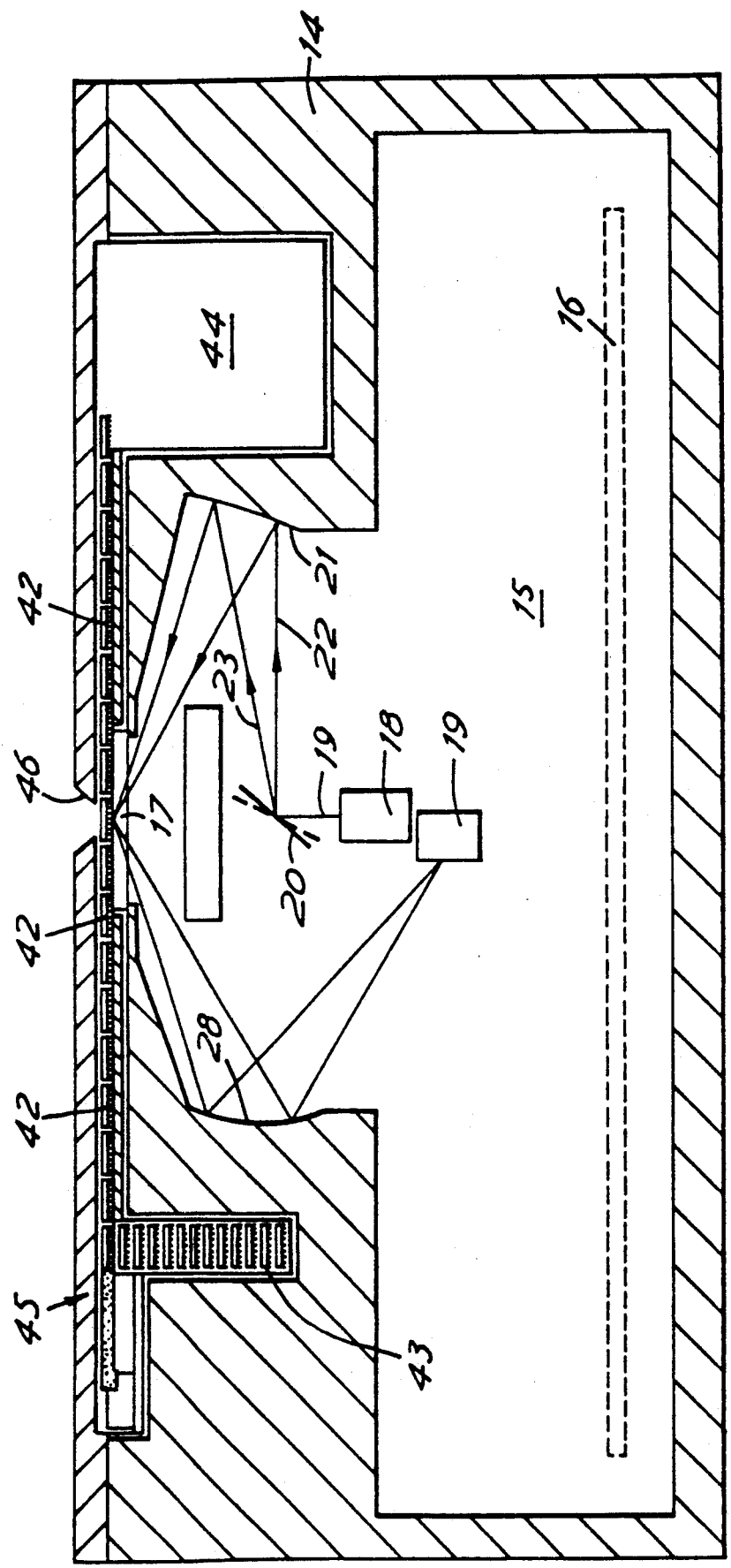
FIG. 7 is a view similar to FIG. 5, showing a second embodiment.

An alternative embodiment of the invention is illustrated in FIG. 7 to which reference will now be made.

In FIG. 7, the continuous film 24 of the embodiment of FIG. 5 is replaced by a disposable element based on a rigid porous material made by Anotec Separation Limited. This material is briefly described above. Because of the brittle nature of the porous material, it is not possible to implement the apparatus in the form of a continuous film. Instead small disposable cards, a few centimeters long, are fed into the machine one by one. Each of these cards comprises a sandwich of a sensitive layer, such as an antibody layer, a metal film layer and the porous layer, this latter being made of any porous material such as the Anotec material. In the operative position one card is positioned on top of the transparent support plate 17 with the porous layer uppermost, and the sensitive layer against the plate 17. The sensitive layer is so thin, typically 50-100 nm thick, that it is effectively transparent to the incident light. The cards, shown under reference 42 are fed from a stack 43, across the transparent support plate 17, to a bin 44. A pusher mechanism 45 acts to push the cards along one by one, and an opening 46 in the top cover 47 of the housing 14 permits the placement of sample on the top surface of the card. Only sample with a relatively high concentration of analyte can be used with this technique because there is no continuous flow of sample past the active area to improve sensitivity.

Because the Anotec material is a honeycomb-like structure, with both it major surface being covered with holes, the layers of metal and antibody will likewise be perforated. As a result, sample applied during a test, and passing through the filter to the surface of the transparent plate 17 will act as a coupling fluid, thus rendering further addition of such fluid unnecessary.

In an alternative embodiment (not shown), an additional structured, e.g. porous, layer is incorporated in the cards of the previous embodiment. The order of layers is: rigid porous (e.g. Anotec) layer—sensitive layer—metal film layer—structural layer. This latter layer can be structured to draw sample fluid through the Anotec filter, thus keeping up a continuous flow during the test, and improving sensitivity. Absorbing pads can be placed at the edges of the cards in order to received used sample directed by said structural layer.

Figure 8:
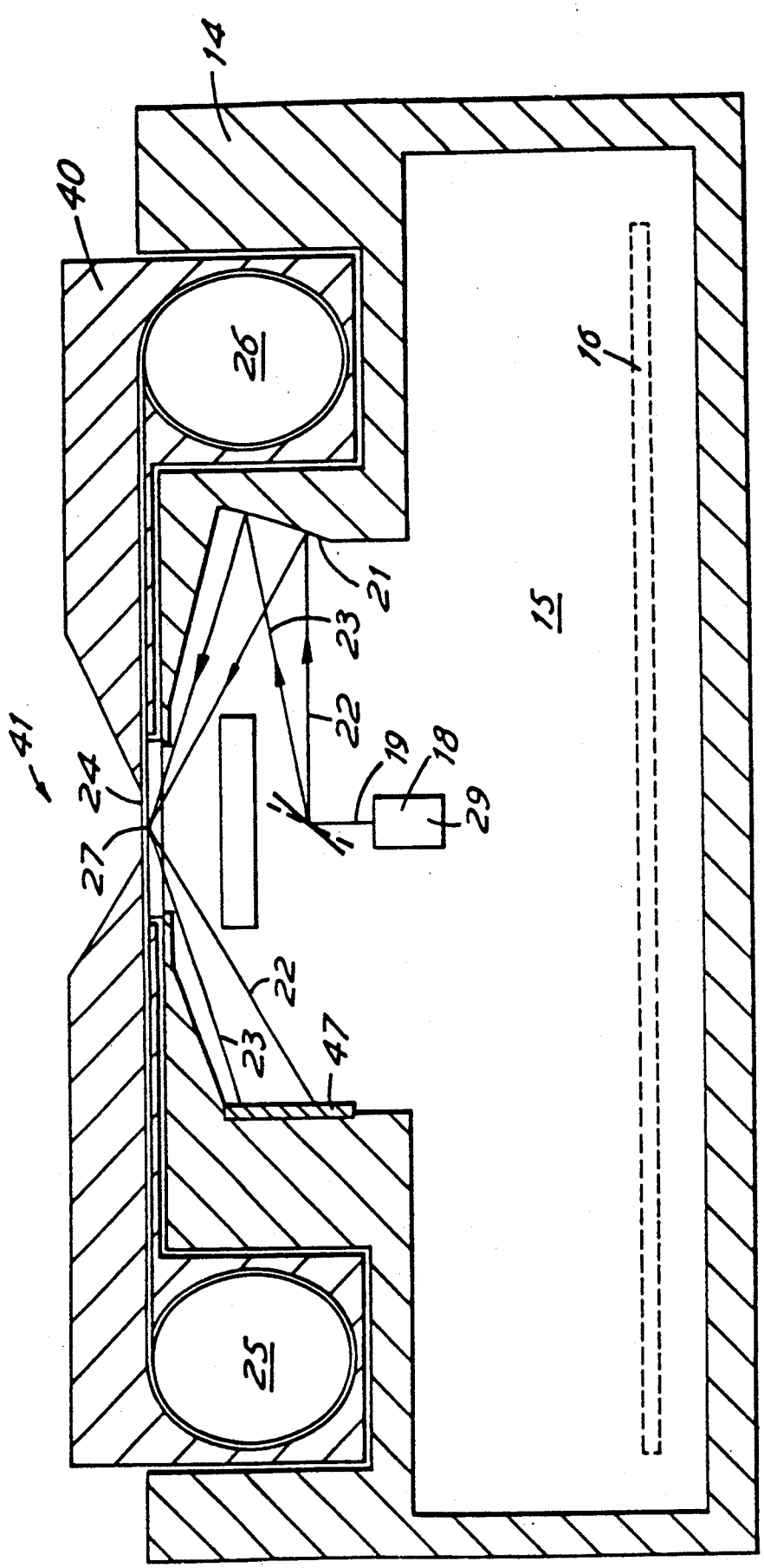
FIG. 8 is a view similar to FIG. 5 showing a third embodiment.

Reference is now made to FIG. 8 which shows an arrangement similar to that of FIG. 5, but in which the output reflecting surface 28 and the small light detector 29 are replaced by a large area light detector 47 such as an amorphous silicon device. The detector may be positioned in any convenient position and has a radiation sensitive area which is large enough to encompass the full movement of the output beam. Once again, the output from the detector is synchronised with the scanning of mirror 20 so that the circuitry is able to identify what the detector is looking at at any one instance of time. For this reason, it is not necessary to provide the detector 47 with any x-y positional detection since the information in the beam is on a time basis, rather than a position basis.

I claim:

1. A sensor for use in biological, biochemical or chemical testing, said sensor comprising a source of electromagnetic radiation for producing a beam of electromagnetic radiation, membrane in the form of a laminate comprising a first film of transparent material, a second film of metal applied to at least part of one surface of said first film and a third film of sensitive material applied to the second film, said membrane further including a sample feeding means whereby the sample to be analyzed is transferred in a controlled manner to said sensitive layer, said sample feeding means comprising a further layer in the laminate comprising said membrane, which further layer is applied to said third film of sensitive material, said further layer being made of a porous material through which a sample may be passed from the side opposite the sensitive layer, in order to react with said sensitive layer, means for directing said beam of electromagnetic radiation into said first film of transparent material in such a way as to be internally reflected off said part of said one surface, and detector means positioned to receive the internally reflected beam, wherein the angle of incidence of said beam at said one surface is such as to cause surface plasmon resonance to occur, the characteristics of which resonance, as detected by the monitoring means, is dependent upon the reaction between the sample and the sensitive layer.

2. The sensor as claimed in claim 1 wherein said membrane is flexible.

3. The sensor as claimed in claim 1 or 2 wherein said membrane is in the form of a semi-continuous film which may be moved between tests to bring a fresh area into use.

4. The sensor as claimed in claim 3 wherein the membrane is package in the form of a cassette.

5. The sensor as claimed in claim 1 further including a block of rigid material transparent to the electromagnetic radiation, and positioned such that said membrane lies against a first surface of said block.

6. The sensor as claimed in claim 5 wherein there is provided an optical coupling fluid between said membrane and said block, such that, in use, the beam enters the block, then passing from the block through said first surface and into said transparent film.

7. The sensor, as claimed in claims 5 or 6 wherein said block is made of a material having the same refractive index as that of said transparent film.

8. The sensor as claimed in claim 1 wherein said further layer takes the form of a structural layer comprising passage means extending from its face remote from the sensitive layer to the opposite face.

9. The sensor as claimed in claim 8 wherein said further layer incorporates an absorbent material which is operable to draw the sample across the sensitive film.

10. The sensor as claimed in claims 8 or 9 wherein a plurality of passage means are provided to enable simultaneous testing of a number of samples, such passage means being spaced apart across the surface of the membrane, and wherein scanning means are provided for scanning the point of incidence of said beam on said one surface across the passage means.

11. The sensor as claimed in claim 10 wherein said sensitive film is not continuous, but takes the form of a plurality of discrete areas of sensitive material applied to said metal film, each of said discrete areas being associated with one of said passage means.

12. A sensor for use in biological, biochemical or chemical testing, said sensor comprising a source of electromagnetic radiation for producing a beam of electromagnetic radiation, a membrane in the form of a laminate comprising a first film of transparent material, a second film of metal applied to at least part of one surface of said first film and a third film of sensitive material applied to the second film, means for introducing onto the sensitive layer so as to react therewith a sample to be analyzed, means for directing said beam of electromagnetic radiation into said first film of transparent material in such a way as to be internally reflected off said part of said one surface, and detector means positioned to receive the internally reflected beam, and wherein the angle of incidence of said beam at said one surface is such as to cause surface plasmon resonance to occur, the characteristics of which resonance, as detected by the monitoring means, is dependent upon the reaction between the sample and the sensitive layer and wherein said sensitive film is not continuous, but takes the form of a plurality of discrete areas of sensitive material applied to said metal film, and wherein scanning means are provided for scanning the point of incidence of said beam on said one surface across said discrete areas.

13. A sensor for use in biological, biochemical or chemical testing, said sensor comprising a source of electromagnetic radiation for producing a beam of electromagnetic radiation, an elongate film in the form of a laminate comprising a first layer of transparent material, a second layer of metal applied to at least part of one surface of said first layer and a third layer of sensitive material applied to the second layer, means for introducing onto the sensitive layer so as to react therewith a sample to be analyzed, means for directing said beam of electromagnetic radiation into said first layer of transparent material in such a way as to be internally reflected off said part of said one surface, detector means positioned to receive the internally reflected beam, and wherein the angle of incidence of said beam at said one surface is such as to cause surface plasmon resonance to occur, the characteristics of which resonance, as detected by the monitoring means, is dependent upon the reaction between the sample and the sensitive layer, and means for moving said film between tests in order to bring a fresh area into use.

* * * * *